United States Patent [19]
Hart et al.

[11] Patent Number: 5,137,628
[45] Date of Patent: Aug. 11, 1992

[54] SEALING ARRANGEMENT FOR A CHROMATOGRAPHY COLUMN

[75] Inventors: Robert L. Hart, Alton, Ill.; David M. Wong, Chester, Mo.

[73] Assignee: Mallinckrodt Medical, Inc., St. Louis, Mo.

[21] Appl. No.: 627,173

[22] Filed: Dec. 14, 1990

Related U.S. Application Data

[62] Division of Ser. No. 481,937, Feb. 20, 1990, Pat. No. 5,089,125.

[51] Int. Cl.⁵ .............................. B01D 15/08
[52] U.S. Cl. .................. 210/198.2; 210/450; 210/456; 55/386
[58] Field of Search ............. 210/198.2, 232, 450, 210/456, 656, 541; 55/386, 67; 422/70

[56] References Cited

U.S. PATENT DOCUMENTS

| | | | |
|---|---|---|---|
| 3,483,986 | 12/1969 | Wright | 210/232 |
| 3,682,315 | 8/1972 | Haller | 210/198.2 |
| 3,763,879 | 10/1973 | Jaworek | 210/198.2 |
| 3,878,099 | 4/1975 | Ogle | 210/198.2 |
| 4,026,803 | 5/1977 | Abrahams | 210/198.2 |
| 4,155,846 | 5/1979 | Novak | 210/198.2 |
| 4,469,496 | 9/1984 | Frischmuth | 55/67 |
| 4,578,193 | 3/1986 | Shepherd | 210/198.2 |
| 4,627,918 | 12/1986 | Saxena | 210/198.2 |
| 4,676,898 | 6/1987 | Saxena | 210/198.2 |
| 4,719,011 | 1/1988 | Shalon | 210/198.2 |
| 4,797,209 | 1/1989 | Jackson | 210/198.2 |
| 4,859,336 | 8/1989 | Savas | 210/472 |
| 4,876,005 | 10/1989 | America | 210/198.2 |
| 4,882,047 | 11/1989 | Shalon | 210/198.2 |

Primary Examiner—Ernest G. Therkorn

[57] ABSTRACT

The present invention relates to chromatography column for process scale high performance purification, which has high stability and structural integrity regardless of the internal diameter or operating pressures. The chromatography column according to the present invention includes a sealing arrangement which enables the production of internally leak proof chromatography columns having large internal diameters at relatively low cost. The present invention also relates to the seal for the chromatography column.

5 Claims, 1 Drawing Sheet

SEALING ARRANGEMENT FOR A CHROMATOGRAPHY COLUMN

This is a division of application Ser. No. 07/481,937 filed Feb. 20, 1990, now U.S. Pat. No. 5,089,125.

BACKGROUND

Chromatography columns have been used for the purification and separation of materials for several years. In particular, chromatography is used to separate mixtures of solutions by selective adsorption packing materials, such as a gelatin, alumina, $C_4$, $C_8$ or $C_{18}$. The selective separation takes place based on the distribution ratios of the components of the mixtures between a mutually immiscible mobile and a fixed stage.

Separation may be carried out by passing a liquid phase mixture to be separated through a column filled with a solid phase material. The solid phase material is chosen so as to retain unwanted components of the liquid phase mixture while allowing desired product components to pass entirely through the column and then collected. The collected components of the liquid phase mixture are obtained in a highly purified state by such separation.

Because of the retention of the unwanted components by the solid phase material, it is necessary to shut down the chromatography column occasionally in order to clean or regenerate the solid phase material and to avoid saturation and inadequate retention. Therefore, it is desirable to maximize the time period between shut downs. One way to extend the time between shut downs is to increase the inside diameter of the chromatography column and thereby give the chromatography column a greater capacity for the solid phase material. Further, by increasing the inside diameter of the chromatography column, capacity can be increased. Therefore, a greater quantity of purified product may be obtained in a smaller amount of time and with a larger time period between shut downs for cleaning.

Known chromatography column are available in a wide range of designs having varying internal diameters. However, commercially available chromatography columns having the required stability and structural integrity for large scale purification processing, generally have had internal diameters of only eight inches or less. While chromatography columns having internal diameters up to twenty four inches have been made, they are not commercially available as off the shelf items because of complex designs which make production so expensive as to be unfeasible. Moreover, such chromatography columns are susceptible to leakage and are generally unsatisfactory in performance, especially at relatively high operating pressures.

OBJECTS OF THE INVENTION

One object of the present invention is to provide a chromatography column for process scale high performance purification, Which has high stability and structural integrity regardless of the internal diameter of the column, the height of the column or the operating pressures.

Another object of the present invention is to provide a chromatography column for process scale high performance purification, which includes a sealing arrangement which enables the production of internally leak proof chromatography columns having large internal diameters and heights.

A further object of the present invention is to provide a chromatography column for process scale high performance purification, which has a simple design and enables construction of chromatography columns having large internal diameters at relatively low cost.

SUMMARY OF THE INVENTION

The above objects are accomplished according to the present invention by a novel sealing arrangement liquid distribution system for chromatography columns, which provides structural integrity, avoids leaking and is relatively inexpensive.

DETAILED DESCRIPTION OF THE INVENTION

Figure 1:
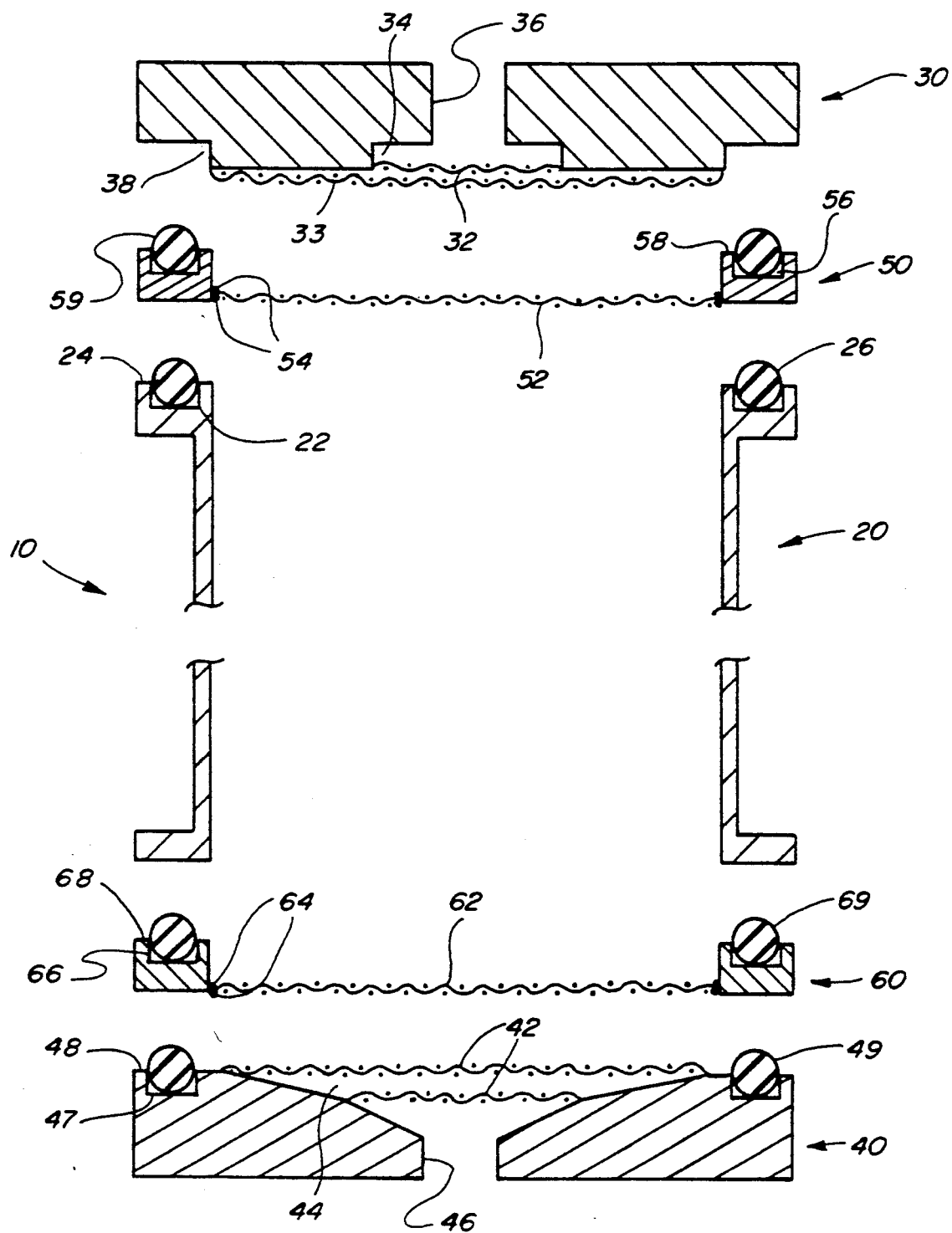
FIG. 1 is a cross-sectional partially out away view of a chromatography column according to the present invention.

FIG. 1 is a cross-sectional partially cut away view of a chromatography column 10, having a main column section 20, an upper column section 30, a lower column section 40, an upper sealing member 50 and a lower sealing member 60. The chromatography column 10, has a generally circular cross-section With a generally circular internal diameter.

The main column section 20, may be constructed of steel; preferably stainless steel, to any desired internal diameter and to withstand any desired operating pressure. In particular, the internal diameter of the main column section 20, may be 24 inches or greater and operating pressures are typically in a range of 230 to 750 psig. However, the columns according to the present invention may be operated at any desired pressure. The main column section 20 is filled with suitable packing material (not shown) for separation, purification and deionization of a component mixture to be processed. A typical packing material is $C_{18}$ packing. The main column section 20, includes a groove 22, in an upper surface 24, for accommodating a sealing O-ring 26.

The upper column section 30, may also be constructed of steel; preferably stainless steel, and includes distribution screens 32, 33, for distributing the component mixture to the packing material. Typically, the distribution screens 32, 33, will be made of stainless steel or another corrosion resistant alloy will be disposed within the upper column section 30. The distribution screen 32, is disposed within a central indented portion 34, of the upper column section 30, while the distribution screen 33, extends along the lower surface of the upper column section 30. An access port 36, is formed through the upper column section 30, and communicates with the central portion 34, to enable addition of the component mixture to the chromatography column 10, and particularly to the distribution screens 32, 33. The upper column section 30, further includes an indented portion 38, which extends around the periphery of the lower surface of the upper column section 30. In particular, the indented portion 38, extends from the sides of the upper column section 30, to a position equivalent to the internal diameter of the main column section 20. The lower surface of the upper column section 30, is slightly inclined from a thick portion adjacent the central indented portion 34, to a thin portion adjacent the indented portion 38, so as to facilitate distribution of the component mixture to the chromatography column 10.

The lower column section 40, is also preferably constructed of stainless steel and includes screens 42, for packing material The screens 42, will preferably be constructed of stainless steel or another corrosion resistant alloy and are disposed within a sloping indented portion 44, of the lower column section 40. The sloping indented portion 44, has an outside diameter corresponding to the internal diameter of the main column section 20, and extends to a centrally located outflow port 46. The slope of the sloping indented portion 44, is adapted to promote drainage from the chromatography column 10. The lower column section 40, further includes a groove 47, in an upper surface 48, for accommodating a sealing O-ring 49.

The upper sealing member 50, comprises a machined steel ring having an internal diameter corresponding to the internal diameter of the main column section 20. A steel frit 52, is disposed in the interior of the upper sealing member 50, and is held in place by welds 54. The sealing member 50, further includes a groove 56, formed in its upper surface 58, which is of a size necessary to accommodate a sealing O-ring 59. The welds 54, completely seal the frit 52, within the interior of upper sealing member 50. In particular, the frit 52, may be attached by silver solder. Thus, leakage around the edges of the frit 52 is completely prevented. Further, because external leaks caused by bad O-rings, improper machining, or the like, are easily detected and corrected, the chromatography columns according to the present invention may be made to be leak free.

The lower sealing member 60 is constructed to be entirely like upper sealing member 50. In particular, lower sealing member 60, is a machined steel ring having an internal diameter corresponding to the internal diameter of the main column section 20. A steel frit 62, is disposed within the interior of lower sealing member 60 and is completely sealed by welds 64, to be leak free around the edges of the frit 62. Lower sealing member 60, also includes a groove 66, in an upper surface 68, for accommodating a sealing O-ring 69.

The multiple O-ring sealing arrangement and welded frits of the present invention enable construction of chromatography columns having large internal diameters while avoiding leakage. In particular, the upper column section 30, and lower column section 40, may be bolted to the main column section 20, with the sealing members 50, 60, inserted therebetween. Upon tightening of the bolts, the O-rings 26, 49, 59, and 69 provide a leak-proof seal for the chromatography column 10. In particular, when the bolts are fully tightened, there exists a metal-to-metal contact between the main column section 20, and the sealing members 50, 60, as well as between the upper sealing member 50, and the upper column section 30, and between the lower sealing member 60, and the lower column section 40. This metal-to-metal contact exists on either side of the respective O-rings, which in turn prevent any leakage through the metal-to metal contact. In combination with the completely leak free welded frits 52, 62, the multiple O-ring sealing structure enables construction of a leak free chromatography column 10, having any desired diameter operating at any desired pressure. Also, the screens 32, 42, lend mechanical support to the first 52, 62, upon full assembly of the chromatography column 10, and thus give more stability and structural integrity to the column 10.

The sealing arrangement of the present invention may be used in any size chromatography column and for any desirable column pressure. The sealing arrangement for the chromatography column according to the present invention large internal diameter chromatography columns. In particular, the chromatography column of the present invention has relatively high stability and structural integrity. Further, the chromatography column of the present invention is leak-proof even at large internal diameters and high operating pressures. Moreover, the chromatography column of the present invention has a simple design and may be constructed for a relatively low cost.

The foregoing has been a description of a preferred embodiment of the present invention. While several specific details have been given, such are only for the propose of explaining the present invention and do not limit the present invention. The scope of the present invention may be ascertained from the following claims.

What is claimed is:

1. A seal for a chromatography column comprising:
   generally ring-shaped main body having an internal diameter corresponding to an internal diameter of said chromatography column and having a groove formed in an upper surface of said main body and a sealing O-ring disposed within said groove;
   a frit suitable for use within a chromatography column disposed within and extending throughout said internal diameter of said main body;
   an upper weld extending around the entire periphery of said frit at a position where an upper surface of said frit contacts interior walls of said main body; and
   a lower weld extending around the entire periphery of said frit at a position where a lower surface of said frit contacts interior walls or said main body.

2. A seal for a chromatography column according to claim 1, wherein said main body and said frit are formed of steel.

3. A seal for a chromatography column according to claim 2, wherein said steel is stainless steel.

4. A seal for a chromatography column according to claim 2, wherein said seal is adapted to fit between the opposing portions of said chromatography column such that said O-ring forms a leak-free seal therebetween.

5. A seal for a chromatography column according to claim 1, wherein said seal is adapted to fit between opposing portions of said chromatography column and form a leak-free seal therebetween.

* * * * *

UNITED STATES PATENT AND TRADEMARK OFFICE
CERTIFICATE OF CORRECTION

PATENT NO. : 5,137,628

DATED : August 11, 1992

INVENTOR(S) : Robert L. Hart, David M. Wong

It is certified that error appears in the above-identified patent and that said Letters Patent is hereby corrected as shown below:

Column 1, line 59
"purification, Which" should be --purification, which--;

Column 2, line 26 "cross-section With" should be --cross-section with--;

Column 3, lines 3,4 "for packing material" should be --for distribution of the material which has passed through the packing material.--;

Column 4, line 5 "first 52" should be --frits 52--;

Column 4, line 13 "present invention large internal" should be --present invention eliminates all the disadvantages associated with known large internal--;

Signed and Sealed this

Fifteenth Day of March, 1994

Attest:

BRUCE LEHMAN

Attesting Officer

Commissioner of Patents and Trademarks